US012685649B2

(12) United States Patent
Miller

(10) Patent No.: US 12,685,649 B2
(45) Date of Patent: Jul. 21, 2026

(54) IMPLANT BEARING REMOVAL GUIDE

(71) Applicant: Zimmer, Inc., Warsaw, IN (US)

(72) Inventor: Kevin Miller, Wakarusa, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 18/828,743

(22) Filed: Sep. 9, 2024

(65) Prior Publication Data

US 2025/0127632 A1     Apr. 24, 2025

Related U.S. Application Data

(60) Provisional application No. 63/591,302, filed on Oct. 18, 2023.

(51) Int. Cl.
    *A61F 2/46*         (2006.01)
    *A61B 17/17*        (2006.01)
(52) U.S. Cl.
    CPC ........ *A61F 2/4612* (2013.01); *A61B 17/1778* (2016.11); *A61F 2002/462* (2013.01); *A61F 2002/4627* (2013.01); *A61F 2002/4641* (2013.01)
(58) Field of Classification Search
    CPC .............. A61F 2/4612; A61F 2002/462; A61F 2002/4641; A61F 2002/4627; A61B 17/1778; A61B 17/1684
    See application file for complete search history.

(56) References Cited

U.S. PATENT DOCUMENTS

| | | | | |
|---|---|---|---|---|
| 4,459,985 | A | * 7/1984 | McKay | A61F 2/461 |
| | | | | 606/100 |
| 5,437,677 | A | 8/1995 | Shearer et al. | |
| 5,702,463 | A | * 12/1997 | Pothier | A61F 2/389 |
| | | | | 623/20.32 |
| 5,769,856 | A | 6/1998 | Dong et al. | |
| 5,800,551 | A | * 9/1998 | Williamson | A61B 17/1778 |
| | | | | 623/19.11 |
| 6,379,386 | B1 * | 4/2002 | Resch | A61B 17/1604 |
| | | | | 623/19.13 |
| 8,197,487 | B2 | 6/2012 | Poncet et al. | |

(Continued)

FOREIGN PATENT DOCUMENTS

| | | |
|---|---|---|
| EP | 2787932 A1 | 10/2014 |
| EP | 2731512 B1 | 10/2020 |

(Continued)

*Primary Examiner* — Matthew J Lawson
(74) *Attorney, Agent, or Firm* — SCHWEGMAN LUNDBERG & WOESSNER, P.A.

(57) ABSTRACT

A drill guide for separation a bearing from a tray of an implant assembly can include a body, a collar, a first projection, a second projection, and a third projection. The body can be engageable with the bearing. The collar can be connected to the body and can define a guide bore configured to guide a drill bit into the bearing when the drill guide is engaged with the bearing. The first projection and the second projection can be engageable with a radially outer surface of the bearing. The third projection can be configured to engage an articulation surface of the bearing to, together with the first projection and the second projection, position the guide bore along a trajectory to guide the drill bit to form a hole in the bearing between the articulation surface and the tray when the bearing is connected to the tray.

18 Claims, 6 Drawing Sheets

(56)          References Cited

U.S. PATENT DOCUMENTS

| | | | |
|---|---|---|---|
| 9,232,955 | B2 | 1/2016 | Bonin, Jr. et al. |
| 9,351,743 | B2 | 5/2016 | Kehres et al. |
| 9,668,759 | B2 | 6/2017 | Strnad et al. |
| 9,763,798 | B2 | 9/2017 | Chavarria et al. |
| 10,010,431 | B2 | 7/2018 | Eraly et al. |
| 10,188,408 | B2 | 1/2019 | Rouyer et al. |
| 10,485,670 | B2 | 11/2019 | Maale |
| 11,419,618 | B2 | 8/2022 | Kehres et al. |
| 11,432,831 | B2 | 9/2022 | Wong et al. |
| 11,458,019 | B2 | 10/2022 | Cleveland et al. |
| 11,771,561 | B2 | 10/2023 | Running et al. |
| 12,458,514 | B2 * | 11/2025 | Wolfe ................... A61F 2/4003 |
| 2005/0015153 | A1 | 1/2005 | Goble et al. |
| 2008/0275457 | A1 * | 11/2008 | Meek ................... A61F 2/4637 |
| | | | 606/99 |
| 2009/0270993 | A1 | 10/2009 | Maisonneuve et al. |
| 2011/0029088 | A1 * | 2/2011 | Rauscher ........... A61B 17/1778 |
| | | | 623/19.11 |
| 2014/0005733 | A1 * | 1/2014 | Matyas ................. A61F 2/4637 |
| | | | 606/86 R |
| 2014/0142578 | A1 | 5/2014 | Hananouchi et al. |
| 2015/0112348 | A1 | 4/2015 | Schoenefeld et al. |
| 2021/0128179 | A1 | 5/2021 | Dupuis et al. |
| 2021/0220151 | A1 * | 7/2021 | Deransart ........... A61B 17/1684 |
| 2021/0338456 | A1 * | 11/2021 | Wolfe ................... A61F 2/4612 |
| 2023/0038980 | A1 * | 2/2023 | Wolfe ................ A61B 17/1778 |
| 2025/0302491 | A1 * | 10/2025 | Ivan ................... A61B 17/1778 |

FOREIGN PATENT DOCUMENTS

| | | | |
|---|---|---|---|
| EP | 3337429 | B1 | 2/2023 |
| EP | 4197497 | A1 | 6/2023 |

* cited by examiner

100

118

116

102

104

106

112

108

100

116

102

108

104

114

106

112

109

110

IMPLANT BEARING REMOVAL GUIDE

CLAIM OF PRIORITY

This application claims the benefit of U.S. Provisional Patent Application Ser. No. 63/591,302, filed on Oct. 18, 2023, the benefit of priority of which is claimed hereby, and which is incorporated by reference herein in its entirety.

BACKGROUND

Implants can be implanted, inserted, or otherwise secured to humans or animals for various purposes. Some implants can be used to replace one or more bones or tissues of a joint that has failed or that no longer provides a full range of motion without pain. For example, in a shoulder that needs to be replaced, the humeral head can be resected, and a replacement head implant can be secured to the humerus and a glenoid implant can be used to replace the glenoid cavity of the scapula. In a reverse shoulder replacement or arthroplasty, a projection can be secured to the scapula and a tray and bearing can be secured to the humerus.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
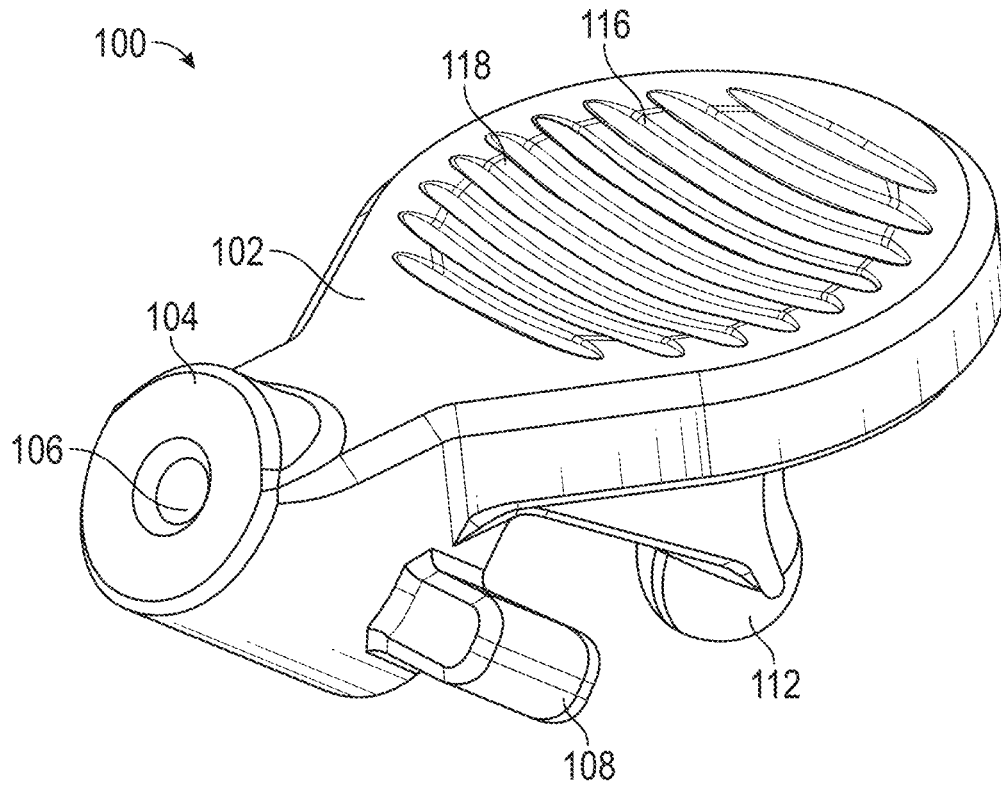
FIG. 1 illustrates an isometric view of a drill guide.

In a reverse shoulder humeral implant assembly, the humeral implant can include a tray that is securable to a resected portion of a proximal portion of the humerus. The tray can include a stem configured for implantation and the tray can be configured (e.g., sized and shaped) to receive a bearing. Optionally, the tray can be connectable to a stem and, optionally, the tray can be connected to a stemless anchor. The bearing can be secured to the tray and can be configured to engage with an implant of the scapula. The bearing can include an articulating wear surface that engages the scapular implant. In some circumstances, it can be required that the bearing be separated from the tray following installation or connection. For example, during a primary surgery the bearing may need to be changed to use a different size or to replace a damaged component. During a revision surgery, the bearing may require replacement to address infection, a failed device, shoulder instability (laxity), or dislocation. However, separation of the bearing from the tray can be relatively difficult. Further, bearings can vary in size and shape to accommodate differences in anatomy from patient to patient, such that it can be difficult to design removal tooling to handle every bearing size.

The present disclosure can help to address these issues by providing a drill guide configured to mate with bearings of various sizes and shapes while providing a drill trajectory that will create a hole in the bearing useful to remove the bearing from the tray, without engaging or damaging the tray during drilling operations. The drill guide can provide these benefits, among others, by including multiple projections that engage multiple portions of the bearing, including the articulation surface, allowing the drill guide to provide a useful drilling trajectory on bearings of various sizes and shapes without using an impactor or generating a large impaction force onto the implant assembly or tray.

For example, a drill guide for separation a bearing from a tray of an implant assembly can include a body, a collar, a first projection, a second projection, and a third projection. The body can be engageable with the bearing. The collar can be connected to the body and can define a guide bore configured to guide a drill bit into the bearing when the drill guide is engaged with the bearing. The first projection and the second projection can be engageable with a radially outer surface of the bearing. The third projection can be configured to engage an articulation surface of the bearing to, together with the first projection and the second projection, position the guide bore along a trajectory to guide the drill bit to form a hole in the bearing between the articulation surface and the tray when the bearing is connected to the tray.

The above discussion is intended to provide an overview of subject matter of the present patent application. It is not intended to provide an exclusive or exhaustive explanation of the invention. The description below is included to provide further information about the present patent application.

Figure 2:
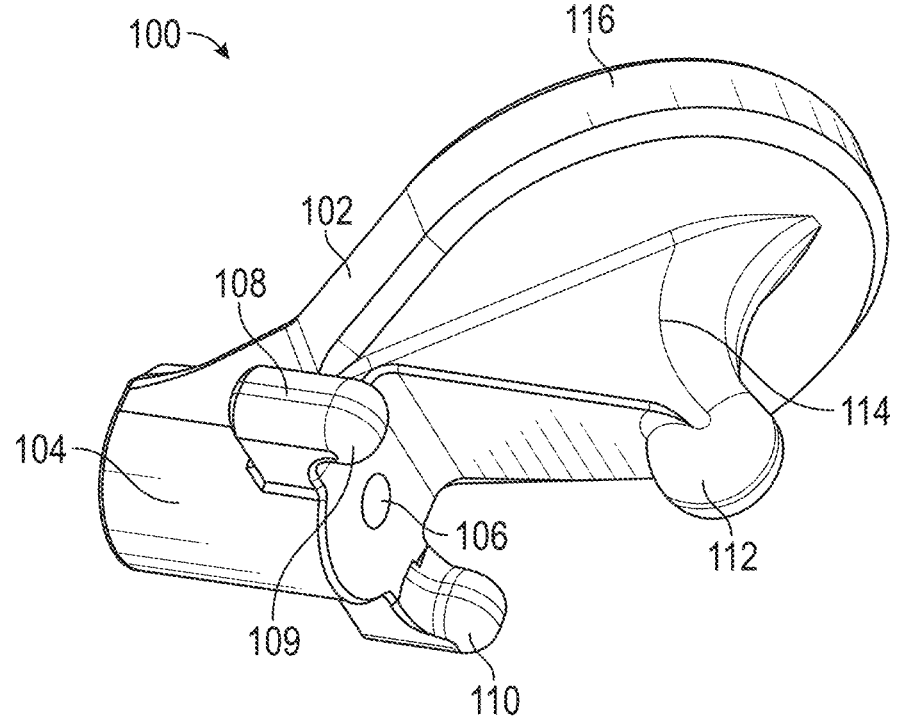
FIG. 2 illustrates an isometric view of a drill guide.

FIG. 1 illustrates an isometric view of a drill guide 100. FIG. 2 illustrates an isometric view of the drill guide 100 and shows orientation indicators Proximal and Distal. The drill guide 100 can be used to position a guide bore along a trajectory to guide a drill bit to form a hole in a bearing between an articulation surface of a bearing and a tray of an implant assembly when the bearing is connected to the tray. The drill guide 100 can be a rigid or semi-rigid body including one or more components that can each be made of materials such as one or more of metals, plastics, foams, elastomers, ceramics, composites, combinations thereof, or the like. Further details of the drill guide 100 are discussed below.

More specifically, the drill guide 100 can include a body 102 that can be configured to support the features of the drill guide 100. The body 102 can be engageable with a bearing to orient the body 102 with respect to the bearing and the tray, as discussed in further detail below. The drill guide 100 can include a collar 104 that can be connected to the body 102 and can define, at least partially, a guide bore 106. Optionally, the body 102 can at least partially define the guide bore 106. The guide bore 106 can be configured to receive and guide a drill bit into a bearing when the drill guide 100 is engaged with the bearing. The collar 104 can be relatively cylindrical in shape, but can have other shapes in other examples.

The drill guide 100 can include a first projection 108 and a second projection 110 that can each be at least partially connected to the collar 104 or can be at least partially connected to the body 102. The first projection 108 and the second projection 110 can extend outward from and parallel to the collar 104 such that the first projection 108 and the second projection 110 are laterally offset from, but aligned with, the collar 104. Each of the first projection 108 and the second projection 110 can be engageable with a radially outer surface of the bearing to help orient the drill guide 100 as discussed in further detail below.

The drill guide 100 can also include a third projection 112 that can be connected to the body 102. The third projection 112 can be configured to engage an articulation surface of the bearing to, together with the first projection 108 and the second projection 110, position the guide bore 106 along a trajectory to guide the drill bit to form a hole in the bearing between the articulation surface and the tray when the bearing is connected to the tray, as discussed in further detail below. The third projection 112 can be connected to the body 102 by a support 114 that can be shaped to limit contact between the support 114 and the bearing when the third projection 112 is engaged with the articulating surface of the bearing, allowing only the third projection 112 to contact the articulation surface and dictate the trajectory of the guide bore 106, and not the support 114 or the body 102.

The drill guide 100 can also include a finger plate 116 connected to the body 102 and forming a curved or concave surface to receive a finger (e.g., a thumb) of a user. The finger plate 116 can allow a user to more easily apply a force to the finger plate 116 and the body 102 to transfer forces to the first projection 108, the second projection 110, or the third projection 112. The finger plate 116 can optionally include serrations 118 that can help to increase friction between the finger of the user and the finger plate 116. The finger plate 116 can include other surface modifications or textures such as one or more of knurling, fluting, grooves, etching, or the like.

Figure 3:
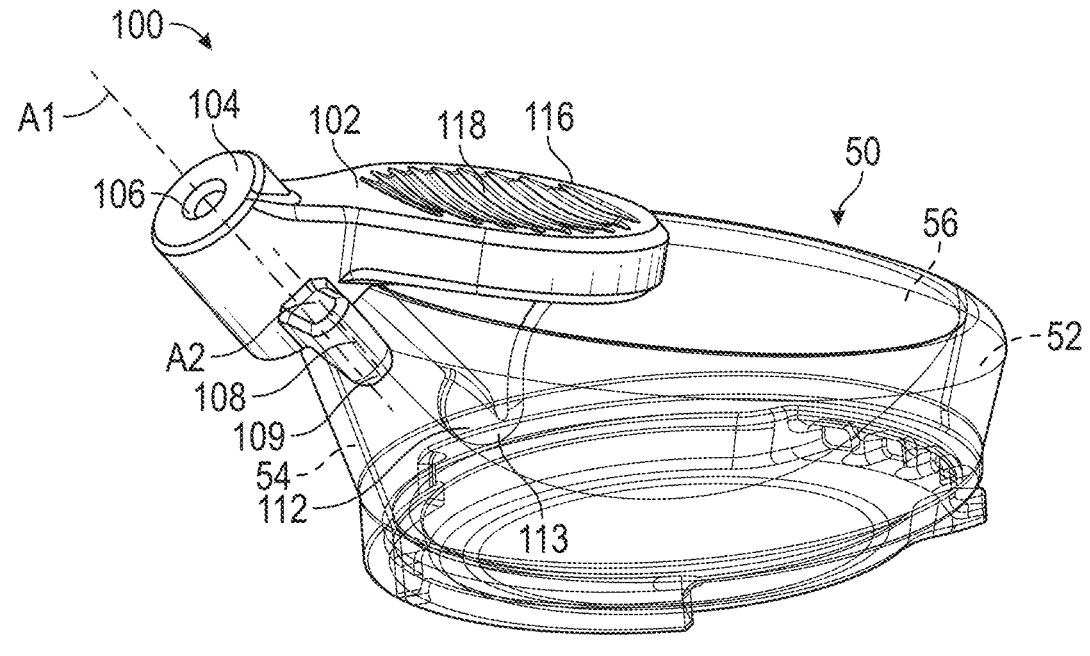
FIG. 3 illustrates an isometric view of a drill guide and a bearing.

FIG. 3 illustrates an isometric view of the drill guide 100 and a bearing 50. The drill guide 100 can be consistent with the drill guide 100 of FIGS. 1 and 2. FIG. 3 shows how the drill guide 100 can interact with the bearing 50. For example, FIG. 3 shows how the body 102 can engage a body 52 of the bearing 50, such as an outer rim. FIG. 3 also shows how the first projection 108 and the second projection 110 can engage a radially outer surface 54 of the bearing 50. FIG. 3 further shows how the third projection 112 can engage an articulation surface 56 of the bearing 50, to position the guide bore 106 along a trajectory to guide the drill bit to form a hole in the bearing between the articulation surface 56 and the tray when the bearing 50 is connected to the tray.

FIG. 3 also shows that the guide bore 206 can define an axis A1 that can be a trajectory for a drill bit that extends therethrough. Also, the first projection 108 and the second projection 110 can each extend from the collar 104 in a direction that is axially offset and axially parallel to the guide bore 106 of the collar 104. For example, as shown in FIG. 3, the first projection 108 can extend from the collar along an axis A2 that can be axially aligned or with the axis A1 or can be parallel to the axis A1. In other examples, the axis A2 can be nearly parallel to the axis A1, such as within 5 degrees, 10 degrees, 15 degrees, or the like. The second projection 110 can extend along an axis A3 (not visible in FIG. 3) that is parallel to or nearly parallel the axes A1 and A2 but laterally offset therefrom.

FIG. 3 also shows that the projections (e.g., the first projection 108) can include a rounded distal portion 109 that can be a portion of the first projection 108 that is engageable with the radially outer surface 54 of the bearing 50. Such a shape can allow for engagement of the projections 108 and 110 at various angles, allowing the first projection 108 and the second projection 110 to transfer force to the radially outer surface 54 of bearings of different sizes. The third projection 112 can also include a distal portion 113 that can have a spherical shape that can be configured to engage the articulation surface 56 of the bearing 50, which can be a curved surface. By being spherical or otherwise rounded, the distal portion 113 can transfer force to the articulation surface of bearings with an articulation surface of various sizes, shapes, or curvatures.

The first projection 108, the second projection 110, or the third projection 112, such as distal portions thereof that are configured to engage the bearing 50 can include one or more surface treatments to increase friction between the projection and the bearing 50 when the drill guide 100 is engaged with the bearing. The surface of the first projection 108, the second projection 110, or the third projection 112 can include knurling, fluting, grooves, etching, bead blasting, other surface treatments, or the like.

Figure 4:
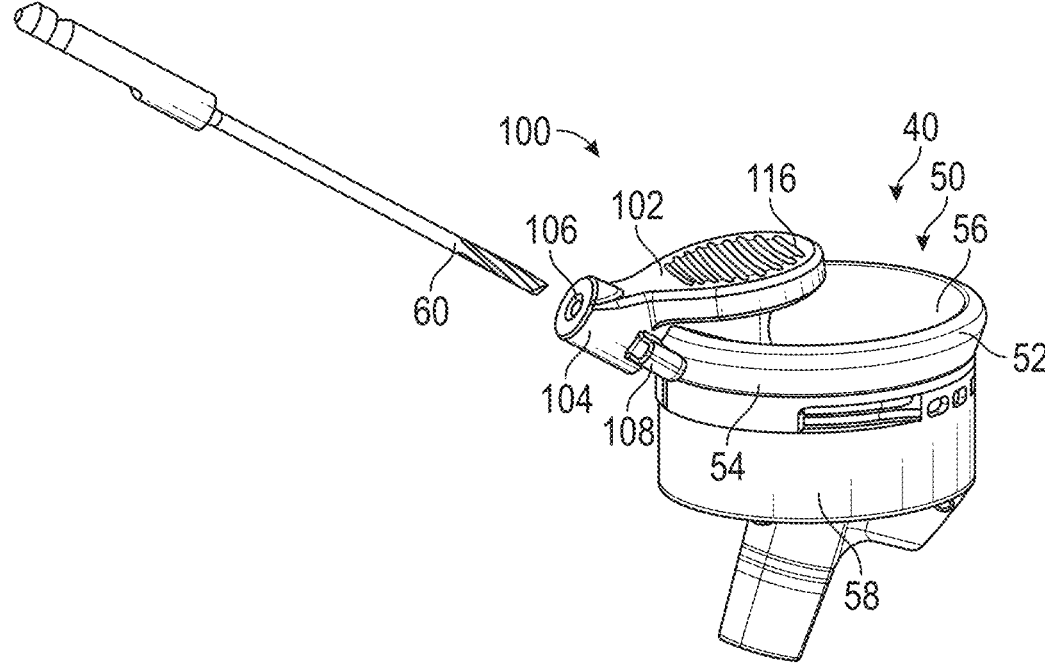
FIG. 4 illustrates an isometric view of a drill guide and an implant assembly.
Figure 5:
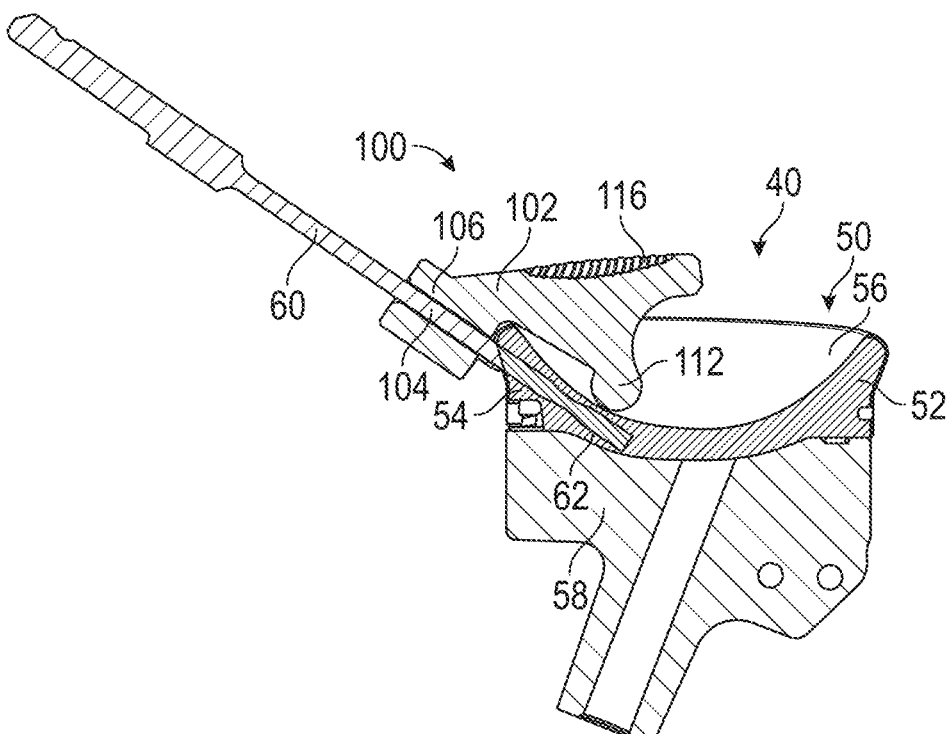
FIG. 5 illustrates a cross-sectional view of a drill guide and an implant assembly.
Figure 6:
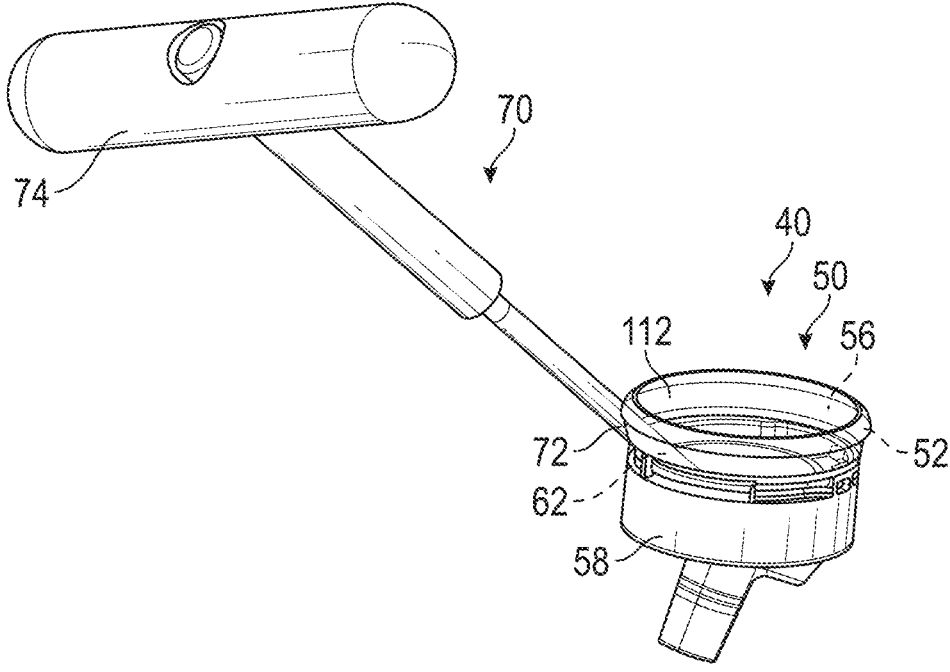
FIG. 6 illustrates an isometric view of a removal instrument and an implant assembly.

FIG. 4 illustrates an isometric view of the drill guide 100 and an implant assembly 40. FIG. 5 illustrates a cross-sectional view of the drill guide 100 and the implant assembly 40. FIG. 6 illustrates an isometric view of a removal instrument and the implant assembly 40. FIGS. 4-6 are discussed together below. The drill guide 100 of FIGS. 4-5 can be consistent with FIGS. 1-3 discussed above, FIGS. 4-5 show additional details of how the drill guide 100 can be used to separate a bearing from a tray.

For example, when it is desired or required to separate the bearing 50 from a tray 58 of the implant assembly 40, the drill guide 100 can be used to guide a drill bit to separate the bearing 50 from the tray 58. Once the drill guide 100 is engaged with the bearing 50 (e.g., the first projection 108 and the second projection 110 engage the radially outer surface 54 and the third projection 112 is engaged with the articulation surface 56) a drill 60 can be inserted into the guide bore 106 to allow the guide bore 106 to guide the drill along a desired trajectory. The trajectory defined by the drill guide 100 can allow the drill 60 to form a hole 62 in the bearing 50 between the articulation surface 56 and between the tray 58 without contacting the tray 58 and without breaking through the articulation surface 56, helping to minimize damage to the tray 58 allowing the same tray to be reused to receive a new bearing. A hole in the bearing 50 along this trajectory can limit damage to the tray 58 while still forming a hole 62 in the bearing 50 that can be used to efficiently and effectively separate the bearing 50 from the tray 58.

As shown in FIG. 6, once the hole 62 is formed in the bearing 50 (by the drill 60, guided by the guide bore 106), a removal tool 70 (or removal instrument or screw) can be used to separate the bearing 50 from the tray 58. A tip 72 of the removal tool 70 can be inserted into the hole 62, such as using a handle 74 of the removal tool 70. The handle 74 can then be operated to rotate the tip 72 within the hole 62. Because the bearing 50 can be connected to the tray 58 through a mechanical interface, such as one or more snap fittings or interfaces, application of forces from within the hole 62 can cause the bearing 50 to separate from the tray 58 without damaging the tray 58.

Figure 7:
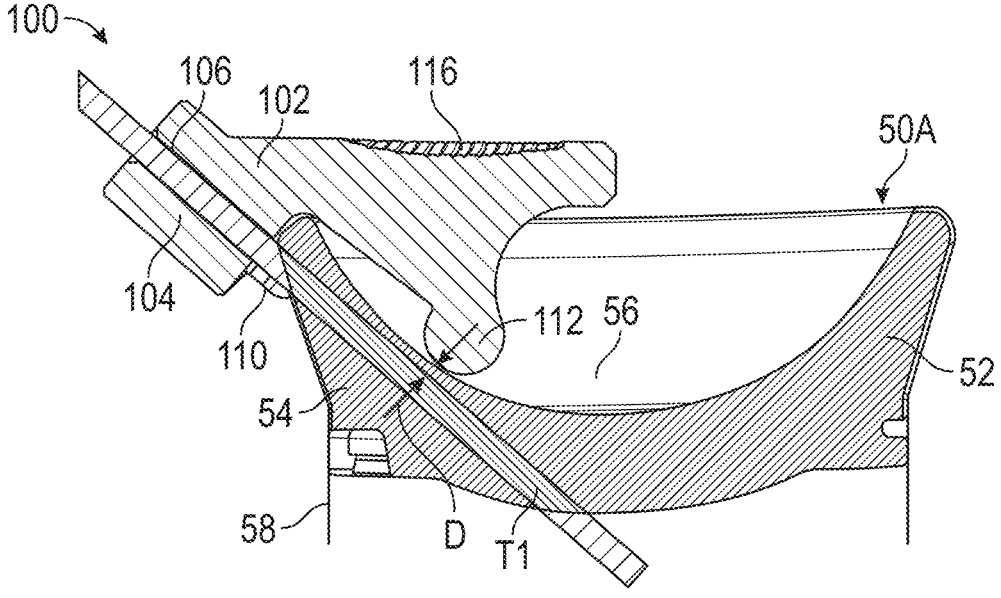
FIG. 7 illustrates a cross-sectional view of a drill guide and a bearing.
Figure 8:
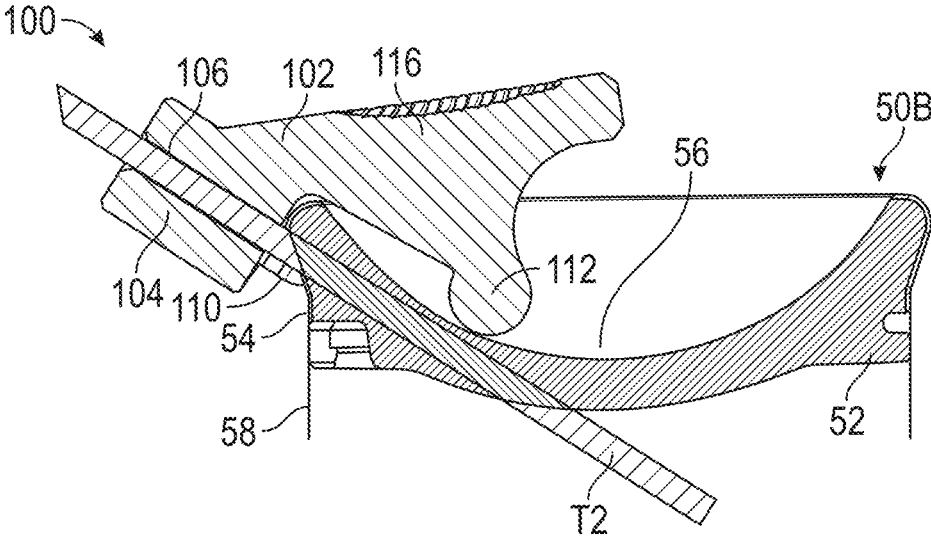
FIG. 8 illustrates a cross-sectional view of a drill guide and a bearing.

FIG. 7 illustrates a cross-sectional view of the drill guide 100 and a bearing 50A. FIG. 8 illustrates a cross-sectional view of the drill guide 100 and a bearing 50B. FIG. 7 also shows trajectory T1 and FIG. 8 shows trajectory T2. FIGS. 7 and 8 are discussed together below. The drill guide 100 of FIGS. 7 and 8 can be consistent with the drill guide 100 discussed above. The bearings 50A and 50B can be similar to the bearing 50 discussed above, but the bearing 50A and the bearing 50B can have different shapes or sizes.

As shown in FIG. 7, the drill guide 100 can be engaged with the bearing 50A such that the first projection 108 and the second projection 110 engage the radially outer surface 54 of the bearing 50A and such that the third projection 112 engages the articulation surface 56 to align the collar 104 and the guide bore 106 such that the guide bore 106 defines a trajectory T1 between the articulation surface 56 and the tray 58, such that a drill bit will form a hole along the trajectory T1 to limit interaction between the drill bit and the articulation surface 56 and between the drill bit and the tray 58.

As shown in FIG. 8, the drill guide 100 can be engaged with the bearing 50B such that the first projection 108 and the second projection 110 engage the radially outer surface 54 of the bearing 50B and such that the third projection 112 engages the articulation surface 56 to align the collar 104 and the guide bore 106 such that the guide bore 106 defines a trajectory T2 between the articulation surface 56 and the tray 58, such that a drill bit will form a hole along the trajectory T2 to limit interaction between the drill bit and the articulation surface 56 and between the drill bit and the tray 58, despite the bearing 50B being relatively smaller and thinner than the bearing 50A. That is, the drill guide 100 can be used to guide the drill bit along a proper trajectory for limiting interaction between the drill bit and the articulation surface 56 and between the drill bit and the tray 58 for bearings of various sizes and shapes.

Also, as shown in FIG. 7, the third projection 112 and the guide bore 106 can be configured such that the third projection 112 is laterally offset from the trajectory T1 by a distance D, which can help to limit interaction between the drill bit and the third projection 112, but can also help to avoid the drill bit from breaking through the articulation surface 56 since the third projection 112 is configured to engage with the articulation surface 56. The distance D can also provide sufficient material for the removal tool 70 (e.g., screw) to engage during separation of the bearing 50 from the tray 58. That is, the distance D (or thickness) can be large enough such that the screw does not break through the articulation surface 56 during screwing operations that separate the bearing 50 from the tray 58. The distance D can be between 0.2 millimeters (mm) and 1.5 MM. In some examples, the distance D can be between 0.4 mm and 1.2 mm. In some examples, the distance D can be between 0.6 mm and 1 mm, such as 0.6 mm, 0.7 mm, 0.8 mm, 0.9 mm, 1 mm, or the like.

Figure 9:
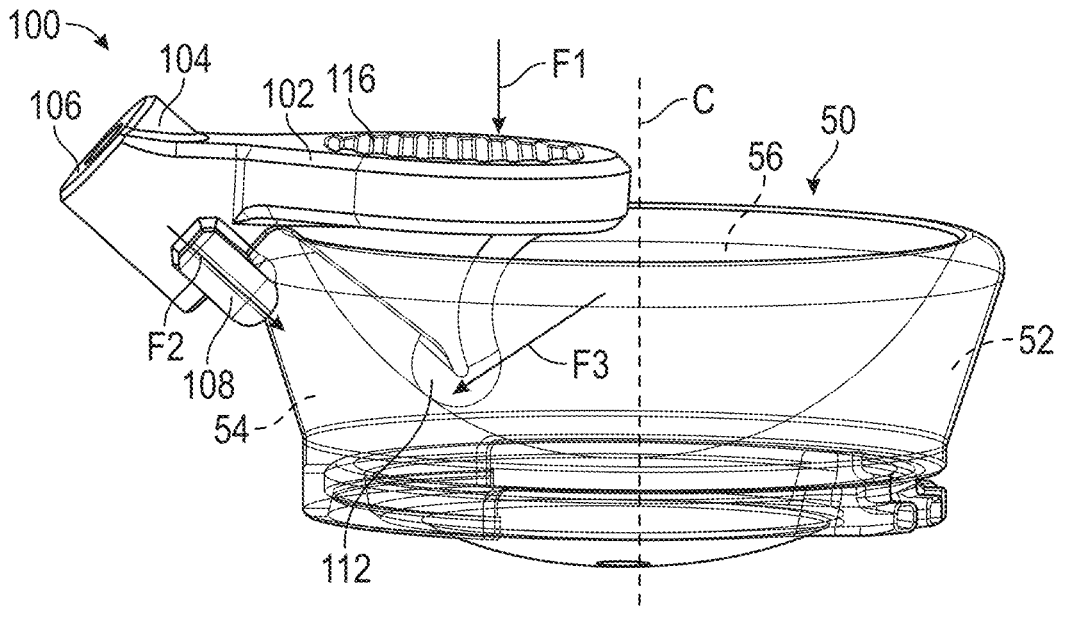
FIG. 9 illustrates an isometric view of a drill guide.

FIG. 9 illustrates an isometric view of the drill guide 100. The drill guide 100 can be similar to the drill guide 100 discussed in FIGS. 1-8 above; FIG. 9 shows further details of operation of the drill guide 100. For example, FIG. 9 shows how a force F1 can be applied to the finger plate 116, such as by a finger or thumb or a user.

Because the finger plate 116 is connected to the body and therefore to the first projection 108, the second projection 110, and the third projection 112, and because the first projection 108, the second projection 110, and the third projection 112 are engaged with the bearing 50, the drill guide 100 can transfer the force F1 from the finger plate 116 to the first projection 108 and the second projection 110 such that the first projection 108 and the second projection 110 each apply a force F2 (only one force shown in FIG. 9) to the radially outer surface 54 where the force F2 can be towards a center plane (or center line) C of the bearing 50.

The drill guide 100 can also transfer the force F1 from the finger plate 116 to the third projection 112 such that the third projection 112 applies a force F3 to the articulation surface 56 where the force 32 can be away from a center plane (or center line) C of the bearing 50 and such that the force F3 is orthogonal or perpendicular to the force F2. In some examples, the force F3 can be towards the force F2 or not parallel to the force F2. Because the forces F2 and F3 are opposing, at least partially, and can be applied to the radially outer surface 54 and the articulation surface 56, which can be at least partially opposing surfaces, the force F1 applied to the finger plate 116 can be transformed or transferred to the projections 108, 110, and 112 to lock or hold the drill guide 100 in place against the bearing 50.

Figure 10:
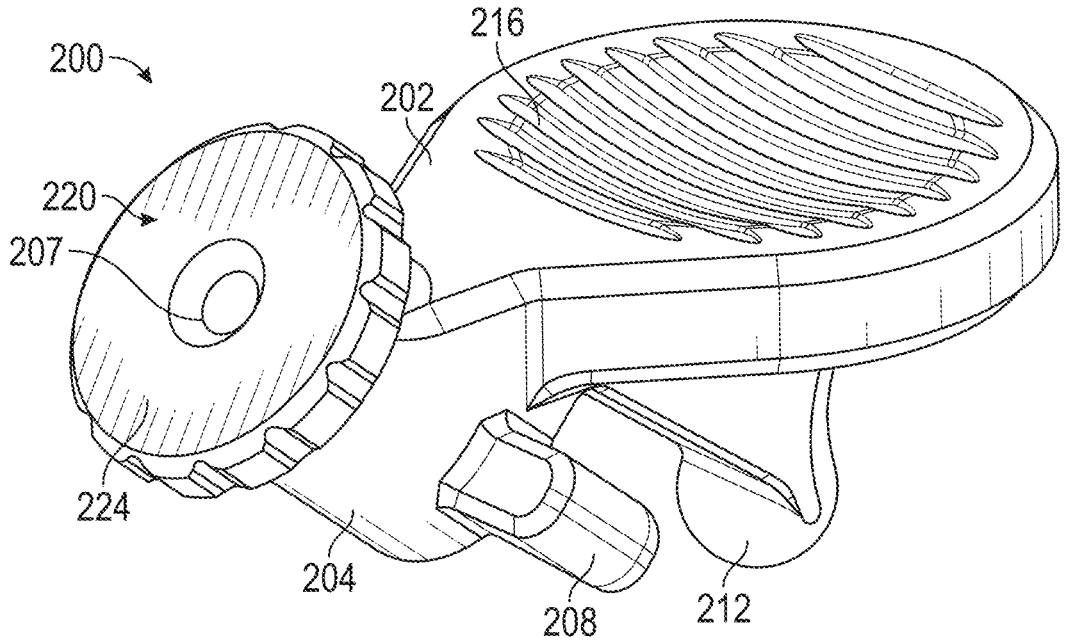
FIG. 10 illustrates an isometric view of a drill guide.
Figure 11:
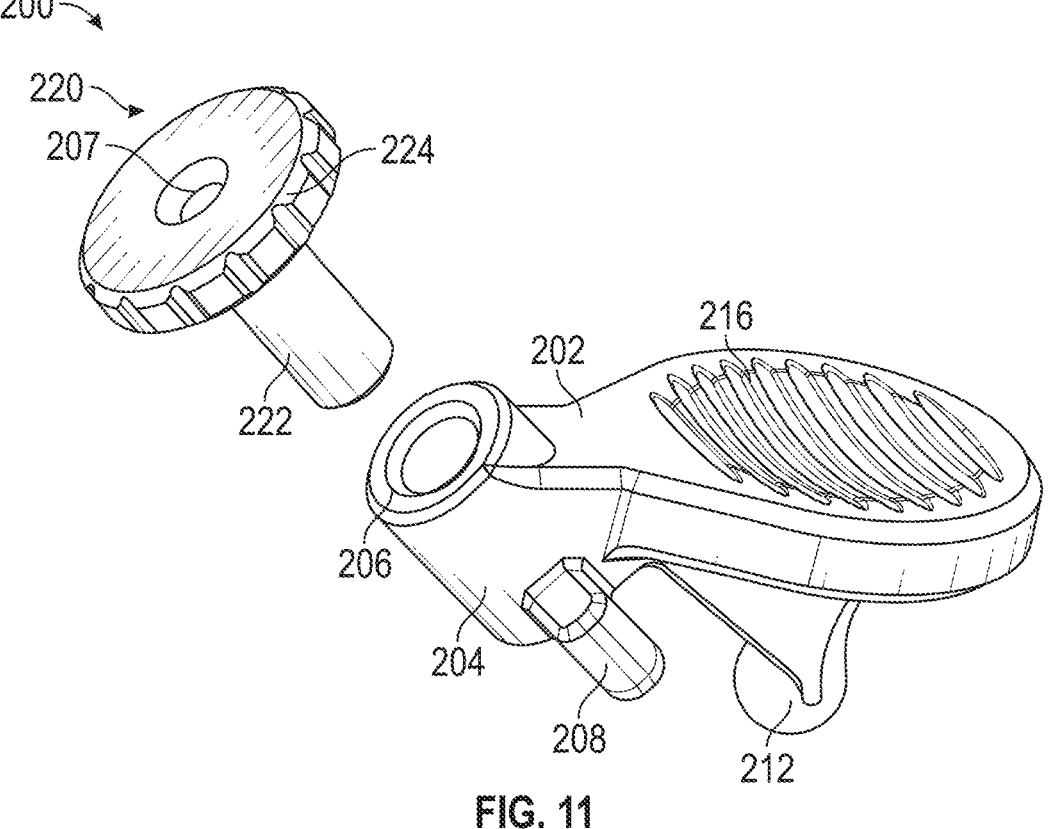
FIG. 11 illustrates an isometric view of a drill guide.

FIG. 10 illustrates an isometric view of a drill guide 200. FIG. 11 illustrates an isometric view of the drill guide 200. FIGS. 10 and 11 are discussed together below. The drill guide 200 can be similar to the drill guide 100 discussed above; the drill guide 200 can include a sleeve insertable into the guide bore where to allow the drill guide 200 to guide both the drill and the screw or removal tool into place. Any of the drill guides discussed above or below can be modified to include the features of the drill guide 200.

Similar to the drill guide 100 discussed above, the drill guide 200 can include a body 202, a collar 204, a guide bore 206, a first projection 208, a second projection 210, a third projection 212, and a finger plate 216. The drill guide 200 can also include a sleeve 220 that can be insertable into the guide bore 206 of the collar 204. The sleeve 220 can also include a drill guide bore 207 that can be configured to guide a drill bit along a desired trajectory, similar to the guide bore 106 discussed above.

More specifically, the collar guide bore 206 can be sized and shaped to receive the tip 72 of the removal tool 70 therein or therethrough such as to help guide insertion of the tip 72 along the desired trajectory for separation of the bearing 50 from the tray 58. The guide bore 206 can also be sized to receive a stem 222 of the sleeve 220. That is, the stem 222 can have an outer diameter that is the same as, or similar to, an outer diameter of the tip 72 of the removal tool 70. As shown in FIG. 11, the sleeve 220 can also include a stop 224 connected to the 222 that can engage the collar 204 to limit insertion of the stem 222 into the guide bore 206. The stop 224 can also be easily manipulated by a user to remove the sleeve 220 from the guide bore 206, such as following a drilling operation.

In operation of some examples, after the drill guide 200 is secured to the bearing 50, the sleeve 220 can be inserted into the guide bore 206. The drill guide bore 207 (defined by the sleeve 220) can be used to receive to receive the drill bit (e.g., the drill 60) at least partially therethrough to guide the drill bit along the trajectory to form the hole (e.g., the hole 62) in the bearing 50. The sleeve 220 can then be removed from the guide bore 206 and the guide bore 206 can receive a screw (e.g., the removal tool 70) at least partially therethrough to guide operation of the removal tool 70 to separate the bearing 50 from the tray 58. The drill guide 200 can, in this way, be used to guide both drilling and separating operations to help ensure the hole is formed correctly and the drilled hole is used correctly.

Notes and Examples

The following, non-limiting examples, detail certain aspects of the present subject matter to solve the challenges and provide the benefits discussed herein, among others.

Example 1 is a drill guide for separation and removal of a bearing from a tray of an implant assembly, the drill guide comprising: a body engageable with the bearing to orient the body with respect to the bearing and the tray; a collar connected to the body and defining a guide bore configured to guide a drill bit into the bearing when the drill guide is engaged with the bearing; a first projection and a second projection engageable with a radially outer surface of the bearing; and a third projection connected to the body and configured to engage an articulation surface of the bearing to, together with the first projection and the second projection, position the guide bore along a trajectory to guide the drill bit to form a hole in the bearing between the articulation surface and the tray when the bearing is connected to the tray.

In Example 2, the subject matter of Example 1 optionally includes wherein the first projection and the second projection are connected to the collar.

In Example 3, the subject matter of Example 2 optionally includes wherein the first projection and the second projection each extend from the collar in a direction that is axially offset and axially parallel to the guide bore of the collar.

In Example 4, the subject matter of any one or more of Examples 2-3 optionally include wherein the first projection and the second projection include a rounded distal portion engageable with the radially outer surface of the bearing.

In Example 5, the subject matter of any one or more of Examples 1~4 optionally include a finger plate connected to the body and configured to: transfer a force from a finger of a user to the first projection and the second projection to the radially outer surface of the bearing; and transfer the force to the third projection to the articulation surface to secure the drill guide to the bearing.

In Example 6, the subject matter of Example 5 optionally includes wherein a first force and a second force transferred by the finger plate to the first projection and the second projection, respectively, to the radially outer surface of the bearing are in a first direction and a second direction, respectively, that are towards a center plane of the bearing and the tray.

In Example 7, the subject matter of Example 6 optionally includes wherein a third force transferred by the finger plate to the third projection to the articulation surface is in a third direction that is away from the center plane of the bearing and the tray.

In Example 8, the subject matter of any one or more of Examples 1-7 optionally include wherein the first projection and the second projection are axially aligned with the guide bore of the collar.

In Example 9, the subject matter of any one or more of Examples 1-8 optionally include wherein the third projection is laterally offset from a drill path of the drill bit when the drill bit is inserted into the guide bore of the collar.

In Example 10, the subject matter of any one or more of Examples 1-9 optionally include a sleeve insertable into the guide bore, the sleeve defining a drill bore to receive the drill bit at least partially therethrough to guide the drill bit along the trajectory, the guide bore configured to receive a screw at least partially therethrough when the sleeve is removed from the guide bore, the screw having a diameter larger than a diameter of the drill bit.

In Example 11, the subject matter of any one or more of Examples 1-10 optionally include wherein a distal portion of the third projection has a spherical shape and is configured to engage a curved surface of the articulation surface of the bearing.

Example 12 is a drill guide for separation and removal of a bearing from a tray of an implant assembly, the drill guide comprising: a body engageable with the bearing to orient the body with respect to the bearing and the tray; a collar connected to the body and defining a guide bore for receiving a drill bit at least partially therethrough to guide the drill bit into the bearing when the drill guide is engaged with the bearing; a first projection and a second projection engageable with a radially outer surface of the bearing; and a third projection connected to the body and configured to engage an articulation surface of the bearing to, together with the first projection and the second projection, position the guide bore along a trajectory to form a hole in the bearing between the articulation surface and the tray.

In Example 13, the subject matter of Example 12 optionally includes wherein the first projection and the second projection each extend from the collar in a direction that is axially offset and axially parallel to the guide bore of the collar.

In Example 14, the subject matter of Example 13 optionally includes wherein the first projection and the second projection include a rounded distal portion engageable with the radially outer surface of the bearing.

In Example 15, the subject matter of any one or more of Examples 12-14 optionally include a finger plate connected to the body and configured to: transfer a force from a finger of a user to the first projection and the second projection to the radially outer surface of the bearing; and transfer the force to the third projection to the articulation surface to secure the drill guide to the bearing.

In Example 16, the subject matter of Example 15 optionally includes wherein a first force and a second force transferred by the finger plate to the first projection and the second projection, respectively, to the radially outer surface of the bearing are in a first direction and a second direction, respectively, that are towards a center plane of the bearing and the tray.

In Example 17, the subject matter of Example 16 optionally includes wherein a third force transferred by the finger plate to the third projection to the articulation surface is in a third direction that is away from the center plane of the bearing and the tray.

In Example 18, the subject matter of any one or more of Examples 12-17 optionally include wherein the first projection and the second projection are axially aligned with the guide bore of the collar, and wherein the third projection is laterally offset from a drill path of the drill bit when the drill bit is inserted into the guide bore of the collar.

In Example 19, the subject matter of any one or more of Examples 12-18 optionally include a sleeve insertable into the guide bore, the sleeve defining a drill bore to receive the drill bit at least partially therethrough to guide the drill bit along the trajectory, the guide bore configured to receive a screw at least partially therethrough when the sleeve is removed from the guide bore, the screw having a diameter larger than a diameter of the drill bit.

In Example 20, the subject matter of any one or more of Examples 12-19 optionally include wherein a distal portion of the third projection has a spherical shape and is configured to engage a curved surface of the articulation surface of the bearing.

In Example 21, the apparatuses or method of any one or any combination of Examples 1-20 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72 (b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A drill guide for separation and removal of a bearing from a tray of an implant assembly, the drill guide comprising:
a body engageable with the bearing to orient the body with respect to the bearing and the tray;
a collar connected to the body and defining a guide bore configured to guide a drill bit into the bearing when the drill guide is engaged with the bearing;
a first projection and a second projection engageable with a radially outer surface of the bearing;
a third projection connected to the body and configured to engage an articulation surface of the bearing to, together with the first projection and the second projection, position the guide bore along a trajectory to guide the drill bit to form a hole in the bearing between the articulation surface and the tray when the bearing is connected to the tray; and
a sleeve insertable into the guide bore, the sleeve defining a drill bore to receive the drill bit at least partially therethrough to guide the drill bit along the trajectory, the guide bore configured to receive a screw at least partially therethrough when the sleeve is removed from the guide bore, the screw having a diameter larger than a diameter of the drill bit.

2. The drill guide of claim 1, wherein the first projection and the second projection are connected to the collar.

3. The drill guide of claim 2, wherein the first projection and the second projection each extend from the collar in a direction that is axially offset and axially parallel to the guide bore of the collar.

4. The drill guide of claim 2, wherein the first projection and the second projection each include a rounded distal portion, individually engageable with the radially outer surface of the bearing.

5. The drill guide of claim 1, comprising:
a finger plate connected to the body and configured to:
transfer a force from a finger of a user to the first projection and the second projection to the radially outer surface of the bearing; and
transfer the force to the third projection to the articulation surface to secure the drill guide to the bearing.

6. The drill guide of claim 5, wherein a first force and a second force transferred by the finger plate to the first projection and the second projection, respectively, to the radially outer surface of the bearing are in a first direction and a second direction, respectively, that are towards a center plane of the bearing and the tray.

7. The drill guide of claim 6, wherein a third force transferred by the finger plate to the third projection to the articulation surface is in a third direction that is away from the center plane of the bearing and the tray.

8. The drill guide of claim 1, wherein the first projection and the second projection are axially aligned with the guide bore of the collar.

9. The drill guide of claim 1, wherein the third projection is laterally offset from a drill path of the drill bit when the drill bit is inserted into the guide bore of the collar.

10. The drill guide of claim 1, wherein a distal portion of the third projection has a spherical shape and is configured to engage a curved surface of the articulation surface of the bearing.

11. A drill guide for separation and removal of a bearing from a tray of an implant assembly, the drill guide comprising:
a body engageable with the bearing to orient the body with respect to the bearing and the tray;

a collar connected to the body and defining a guide bore for receiving a drill bit at least partially therethrough to guide the drill bit into the bearing when the drill guide is engaged with the bearing;

a first projection and a second projection engageable with a radially outer surface of the bearing;

a third projection connected to the body and configured to engage an articulation surface of the bearing to, together with the first projection and the second projection, position the guide bore along a trajectory to form a hole in the bearing between the articulation surface and the tray; and a sleeve insertable into the guide bore, the sleeve defining a drill bore to receive the drill bit at least partially therethrough to guide the drill bit along the trajectory, the guide bore configured to receive a screw at least partially therethrough when the sleeve is removed from the guide bore, the screw having a diameter larger than a diameter of the drill bit.

12. The drill guide of claim 11, wherein the first projection and the second projection each extend from the collar in a direction that is axially offset and axially parallel to the guide bore of the collar.

13. The drill guide of claim 12, wherein the first projection and the second projection include a rounded distal portion engageable with the radially outer surface of the bearing.

14. The drill guide of claim 12, comprising:

a finger plate connected to the body and configured to:

transfer a force from a finger of a user to the first projection and the second projection to the radially outer surface of the bearing; and transfer the force to the third projection to the articulation surface to secure the drill guide to the bearing.

15. The drill guide of claim 14, wherein a first force and a second force transferred by the finger plate to the first projection and the second projection, respectively, to the radially outer surface of the bearing are in a first direction and a second direction, respectively, that are towards a center plane of the bearing and the tray.

16. The drill guide of claim 15, wherein a third force transferred by the finger plate to the third projection to the articulation surface is in a third direction that is away from the center plane of the bearing and the tray.

17. The drill guide of claim 11, wherein the first projection and the second projection are axially aligned with the guide bore of the collar, and wherein the third projection is laterally offset from a drill path of the drill bit when the drill bit is inserted into the guide bore of the collar.

18. The drill guide of claim 11, wherein a distal portion of the third projection has a spherical shape and is configured to engage a curved surface of the articulation surface of the bearing.

\* \* \* \* \*